United States Patent [19]

Whitaker

[11] Patent Number: 5,197,941
[45] Date of Patent: Mar. 30, 1993

[54] PORTABLE DEVICE FOR CONTROLLING CIRCADIAN RHYTHM DISORDERS

[76] Inventor: Barbara Whitaker, 526 Meadows Dr., Glendale, Calif. 91202

[21] Appl. No.: 737,670

[22] Filed: Jul. 30, 1991

[51] Int. Cl.$^5$ ............................................. A61M 21/00
[52] U.S. Cl. .................................... 600/27; 128/419 N
[58] Field of Search .................................. 600/26–78; 128/419 N

[56] References Cited

U.S. PATENT DOCUMENTS

| | | |
|---|---|---|
| 2,843,111 | 7/1958 | Roll . |
| 3,576,185 | 4/1971 | Schulz et al. . |
| 3,727,395 | 4/1973 | Baylor . |
| 3,798,889 | 3/1974 | Chadwick . |
| 3,826,250 | 7/1974 | Adams .................................. 600/28 |
| 4,028,882 | 6/1977 | Muncheryan . |
| 4,093,944 | 6/1978 | Muncheryan .......................... 600/28 |
| 4,289,121 | 9/1981 | Kupriyanovich et al. . |
| 4,893,615 | 1/1990 | Khabirova ............................. 600/28 |

FOREIGN PATENT DOCUMENTS

| | | | |
|---|---|---|---|
| 0322635 | 7/1989 | European Pat. Off. ........ | 128/419 N |
| 3607235 | 9/1987 | Fed. Rep. of Germany ... | 128/419 N |

Primary Examiner—Lee S. Cohen
Assistant Examiner—John P. Lacyk
Attorney, Agent, or Firm—Norman B. Rainer

[57] ABSTRACT

A therapeutic system for modifying a person's circadian rhythms employs components which generate physical factors such as light, sound and airborne negative ions which are caused to contact the person. The generation of the physical factors occurs in manually or electronically controllable intensities and durations at cyclic intervals of variable length.

2 Claims, 2 Drawing Sheets

PORTABLE DEVICE FOR CONTROLLING CIRCADIAN RHYTHM DISORDERS

BACKGROUND OF THE INVENTION

1. Field of the Invention

This invention relates to the manipulation of Circadian Rhythms in an individual for therapeutic purposes and more particularly concerns a device for enhancing sleep by increasing negative ions and introducing light or gradually increasing intensity for the duration of a treatment period.

2. Description of the Prior Art

Disturbances of an individual's natural patterns of sleep/wake cycles and the demands of the environment are common. Rotating shift schedules, travel across time zones, and other disruptions to a regular sleep schedule impose considerable demands on "biological clocks" and may result in symptoms including sleep disturbances, mood disturbance, irritability, lack of motivation and loss of energy, increasing to depression, etc. Most people have some degree of sleepiness following a period of light or sleep deprivation, particularly when crossing multiple time zones. Substance abuse, including that caused by excessive caffeine, alcohol, or sedatives may become self-defeating solutions to schedule problems. Sleep/wake schedule problems, and their sequelae, may sufficiently disrupt or cause symptomatology to warrant psychiatric consultation. Among patients who already have psychiatric disorders, such schedule problems may aggravate the underlying disorder and make management more difficult.

Many have observed that certain people suffer from a full depression or exhibit depressive symptoms during the winter months and have spontaneous recovery during the spring. Such mood disorders, known as Seasonal Affective Disorders (SAD), appear to be related to seasonal variations of light. Regular appearance of the disorder usually occurs between the beginning of October and the end of November in the northern hemisphere.

Researchers have determined that such disorders may be caused by disturbances in the individual's Circadian Rhythms (C.R.). The biological clock regulates the individual's 24-hour entrainment to the Earth's cycle. A modality for treating SAD and other sleep/wake disorders has earlier been developed, and is commonly referred to as phototherapy.

Phototherapy involves the manipulation of light in order to advance or delay the phase of the Circadian Rhythm. Since the primary disturbance centers around diminished light sources, the treatment requires restoration of light to re-set the biological clock. To ensure optimal response, the phototherapy must be given the following considerations: optimal timing, duration of light exposure, intensity of light, individual selectivity, frequency and number of treatment sessions, and availability. It has further been established that certain sounds and ion generation may be employed during treatment sessions to improve the results of the phototherapy.

Treatment centers have been established for phototherapy. These centers require daily attendance by the individual. Due to the aforementioned considerations, the regimen is difficult to adapt to different individuals' needs. Treatment centers are not always available to travelers who cross multiple time zones regularly. Moreover, phototherapy as prescribed in treatment centers is expensive and must be maintained at regular intervals, or relapses will occur. Furthermore, optimal treatment intervals may occur at times immediately preceding and following periods of sleep. The interval of time between sleep and treatment may adversely effect the results of such treatment. The timing of such exposure is of major importance. Morning light tends to advance the C.R. and evening light tends to delay the C.R. Mid day light exposure has been shown to have little effect on the C.R.

Various devices have been disclosed in the prior art which are designed to induce sleep or awaken an individual. The device disclosed in U.S. Pat. No. 3,798,889 utilizes a rheostat and motor arrangement to gradually increase light from a lamp, thereby awakening an individual. However, this device has no adjustability of the rate at which the level is increased, and makes no provision for the gradual dimming of the lamp. The device disclosed in U.S. Pat. No. 3,727,395 is designed to gradually dim a lamp in order to induce sleep, and provides no phototherapy means. U.S. Pat. No. 2,843,111 similarly provides a device which dims light gradually, and further utilizes a simple music box. The music is played at a constant volume to help induce sleep.

Although each of the aforesaid devices are designed to induce sleep or awakening, they are quite limited in their respective intended usages. In order to yield the desired results of modification of Circadian Rhythms, it is necessary to have complete adjustability of timing, rate of increase of full spectrum light at a therapeutic intensity and duration. Furthermore, none of the prior art devices teach the principle of the combined effect of sound, negative ion generation and light for use in advancing or delaying an individual's biological clock.

It is therefore an object of the present invention to provide means for manipulating an individual's Circadian Rhythm by systematically advancing or delaying the individual's sleep/wake cycle.

It is a further object of this invention to provide a device for gradually increasing the level of light exposed to an individual at a programmable intensity, during the dark adapted interval.

It is yet another object of the present invention to provide a device of the aforesaid nature capable of producing controlled relaxing sounds at a pre-programmed frequency.

It is still another object of the present invention to provide a device of the aforesaid nature capable of generating negative ions at a programmable interval and duration.

It is still another object of the present invention to provide a device of the aforesaid nature which is portable, easy to operate, of durable construction, and amenable to low cost manufacture.

SUMMARY OF THE INVENTION

The above and other beneficial objects of the present invention are accomplished in accordance with the present invention by an electronic system adapted to programmably increase the level of light, sound, and airborne negative ions exposed to an individual for the therapeutic purpose of modifying the individual's Circadian Rhythms, said system comprised of:

a) power supply means adapted to receive line current input voltages to be used throughout said system, b) a clock module having an operator adjustable wake time at which said clock module initiates a light output cycle, c) an up ramp module having current input and output means and adapted to be initiated by the light output cycle of said clock module, said up ramp module adapted to controllably increase its output from zero to 100% of said input current, over an operator adjustable wake duration, d) a sleep function module activated by said individual at the beginning of a desired sleep period, and having a sleep cycle output, e) a down ramp module having current input and output means and adapted to be initiated by said sleep cycle output, said down ramp module adapted to controllably decrease its output from 100% of said input current to zero, over an operator adjustable sleep function duration, f) a lamp control module having an input terminal adapted to receive line current, and a control terminal adapted to receive current from said up ramp module, said lamp control module adapted to vary the line current in response to output currents from said up ramp module, g) a lamp adapted to receive current from said lamp control module and provide light exposure to said individual, h) sound generator module adapted to receive line current and be activated by a control signal from the output means of said down ramp module, said sound generator adapted to create an audio output signal, i) speaker means adapted to receive said audio output signal and generate audible sound, j) an ion generator module having a line input and adapted to be activated by a control signal from said clock module or said sleep function module, and thereby toggle an ion generator output signal on and off, k) ion generator means adapted to be toggled on and off by said ion generator output signal, said ion generator adapted to provide exposure of said individual to a stream of ionized air, and l) housing means adapted to protectively enclose said system. In a preferred embodiment, switch means may be employed to override control of lamp, sound, and ion generation. The duration and ramp times of the up ramp and down ramp modules may be operator adjustable.

The housing means may have reflector means for directing the generated light at eye level of the individual.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing.

DESCRIPTION OF THE PREFERRED EMBODIMENT

Figure 1:
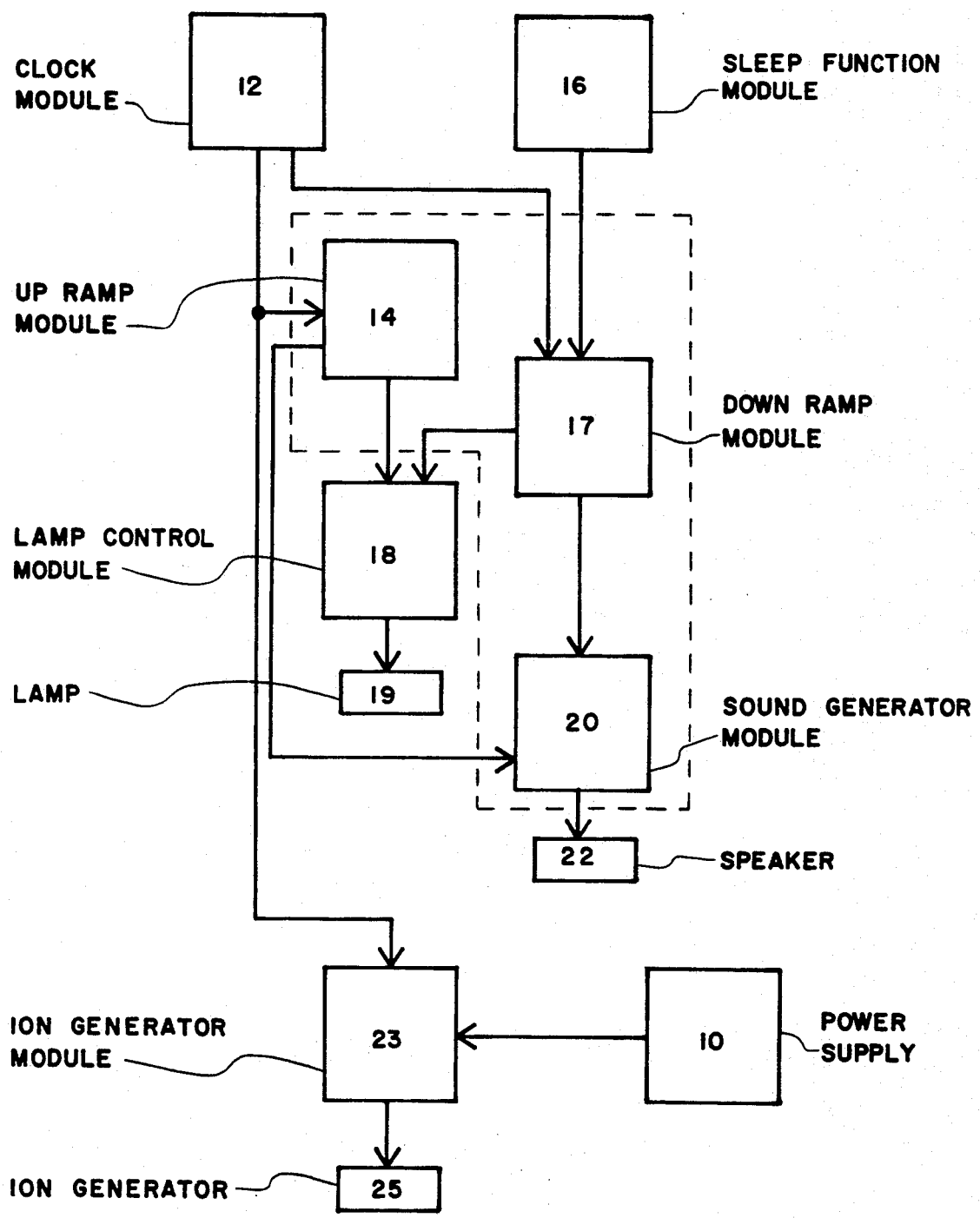
FIG. 1 is a block diagram of an embodiment of the system of the present invention.
Figure 2:
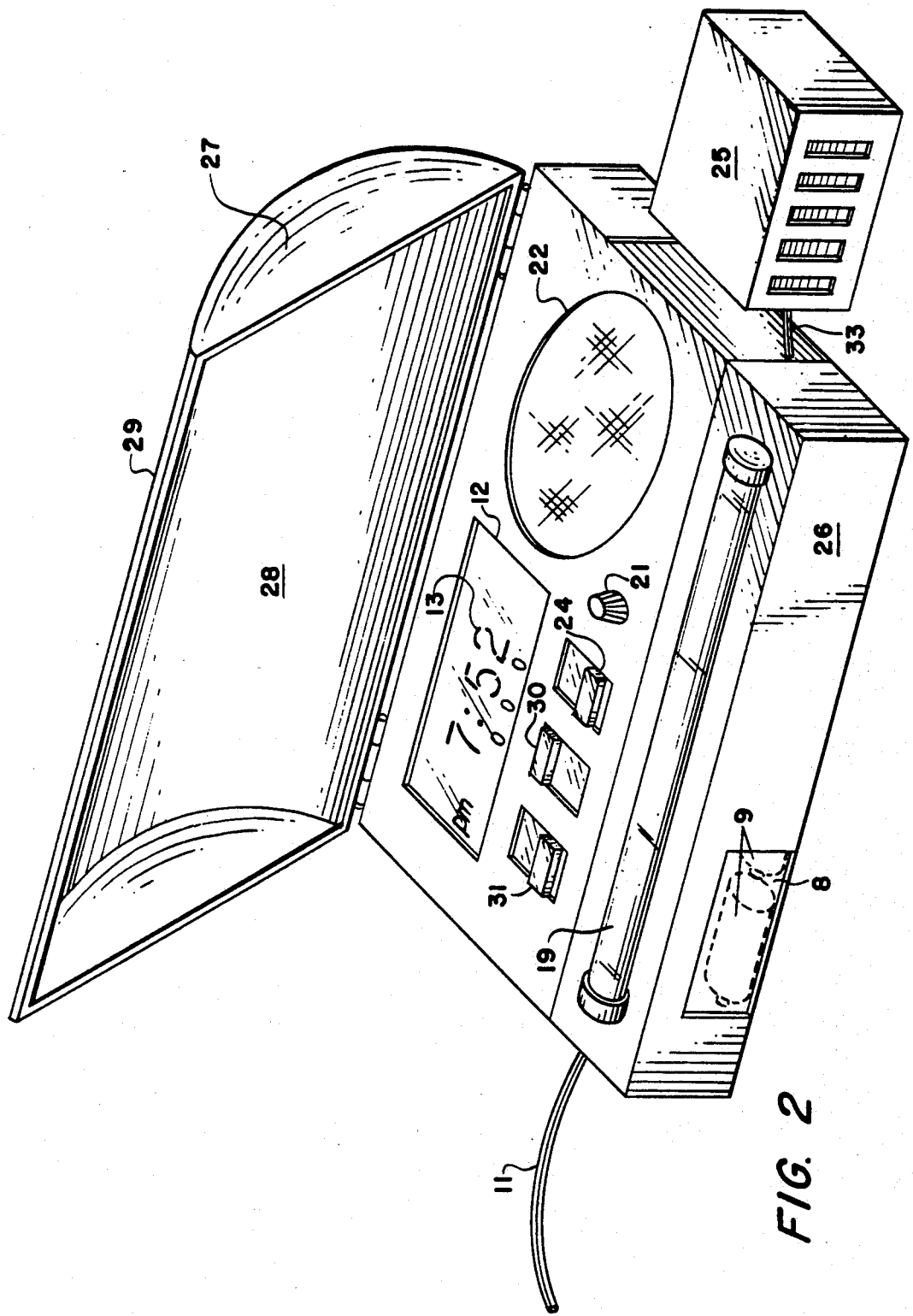
FIG. 2 is a perspective view of the embodiment of a device incorporating the system of FIG. 1.

Referring to FIGS. 1-2, an embodiment of the therapeutic device of the present invention is shown in the form of an electronic system adapted to programmably increase and decrease the level of light, sound, and airborne ions exposed to an individual for the purpose of modifying the individual's Circadian Rhythms. The device is energized by power supply means 10 preferably adapted to receive a variety of current input voltages through power cord 11, or batteries 8, stored in compartment 9, and convert current to a regulated current output of +5 VDC, +12 VDC, or −12 VDC by means of voltage regulators models 7805, 7812, and 7912. These regulated currents are used throughout the system's integrated circuitry. Power cord 11 also provides 120 VAC line current for the operation of various components.

Clock module 12 is a digital clock circuit such as the programmable clock module MA 1020M manufactured by III V Semiconductor, Inc. The clock has a 0.84 inch height digital display 13 and an operator adjustable wake time at which clock 12 initiates a light output cycle.

Up ramp means 14 utilizes a Zilog Z-80 8-bit microprocessor 15 which receives a 5 VDC signal from the output of clock 12. Ramp means 14 outputs a lamp control pulsed signal adapted to controllably increase from zero to 100% of its input current over an operator adjustable light duration, typically of 5 minutes. The duration of 100% output may be adjusted between 30 60, and 90 minutes.

Sleep function module 16 is activated by the individual at the beginning of a desired sleep period by means of switch 31 and has a sleep cycle output. Down ramp means 17 has current input and output means from microprocessor 15, and is adapted to be initiated by said sleep cycle output, or output from clock module 12. Down ramp means 17 is further adapted to controllably decrease its output from 100% of input current to zero, over an operator adjustable sleep function duration, typically between 0 and 60 minutes.

Lamp control module 18 has an input terminal adapted to receive line current and a control terminal adapted to receive pulses from up ramp and down ramp means 14 and 17, respectively, as output from microprocessor 15. Lamp control module 18 utilizes phase control of a thyristor bridge circuit to vary the line current from an output terminal, as controlled by the pulsed output of microprocessor 15. Lamp 19 is adapted to receive current from lamp control module 18 and provide light exposure to the individual. Lamp 19 may be in the form of a full spectrum socketed bulb or elongated full spectrum tube having a 500 lux output. Lamp control module 18 is equipped with override switch 30 which will allow the individual to independently turn lamp 19 on and off.

Sound generator module 20 is adapted to receive line current and be activated by a pulsed control signal from the output means of up ramp module 14 or down ramp module 17. Module 20 utilizes microprocessor 15 as a controlling element and also contains volume control 21. Module 20 utilizes an AY-3-8910A programmable sound generator to create an audio output signal. Speaker means 22 is adapted to receive the audio output signal and generate audible sound of controllable volume and tone.

Ion generator module 23 has a line input and is adapted to be activated by a pulsed control signal from clock module 12 and thereby toggle an ion output signal on and off. Module 23 is also equipped with override switch 24 which will provide independent control of the output signal. Ion generator means 25 is adapted to be toggled on and off by the ion output signal and is adapted to provide exposure of the individual to a stream of ionized air. Suitable ion generator means 25 may be, for example, those manufactured by Vortex, Wein Lo., or Pollenex.

Housing means in the form of thermoplastic injection molded box 26 is adapted to protectively enclose the system. Lid 27 is hingedly associated with box 26 and has a reflective surface 28 associated with an interior surface 29. Surface 28 may be pivoted in order to direct light from lamp 19 upon the face of an individual lying or sitting in close proximity to the system. The ion generator 25 may be remotely positionable with respect to box 26 by virtue of extension cord 33.

The system may be adjusted by the individual being treated. Adjustment is accomplished by setting clock 12 and microprocessor 15 to a program which will advance or delay the individual's Circadian Rhythm. Clock module 12 yields individual control of light, sound, and ion functions. Upon retiring, the individual will activate the system by means of sleep function module 16. At individual programmed intervals, lamp 19 may be programmed via clock module 12 to illuminate at 100% intensity, and 1/f chirping sounds will be emitted from speaker means 22. Ionized air will flow from ion generator 25, upon initiation from clock module 12, for a preprogrammed interval. As the time progresses, down ramp means 17 will utilize microprocessor 15, and sound generator module 20 to gradually decrease sound volume to zero. At the programmed wake time, up ramp means 14 utilizes microprocessor 15 and lamp control module 18 to gradually increase light intensity to 100% for preprogrammed treatment duration. Then, clock module 12 will utilize microprocessor 15 to down-ramp lamp 19 from 100% intensity to zero intensity.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described my invention, what is claimed is:

1. A system for programmably varying the levels of light, sound, and airborne negative ions exposed to an individual for the therapeutic purpose of modifying the individual's Circadian Rhythms, said system comprised of the following elements:

a) power supply means adapted to receive line current input voltages to be used throughout said system,
   b) a clock module having an operator adjustable wake time at which said clock module initiates a light output cycle,
   c) an up ramp module having current input and output means and adapted to be initiated by the light output cycle of said clock module, said up ramp module adapted to controllably increase its output means from zero to 100% of said input current, over an operator adjustable wake duration,
   d) a sleep function module activated by said individual at the beginning of the desired sleep period, and having a sleep cycle output interactive with a down ramp module,
   e) said down ramp module having current input and output means and adapted to be initiated by said sleep cycle output, said down ramp module adapted to controllably decrease its output means from 100% of said input current to zero over an operator adjustable sleep function duration,
   f) a lamp control module having an input terminal adapted to receive line current, and a control terminal adapted to receive current from said up ramp and down ramp modules, said lamp control module adapted to vary the line current in response to current received from said up and down ramp modules,
   g) a lamp receiving current from said lamp control module and providing light exposure to said individual,
   h) a sound generator module adapted to receive line current and be activated by control signals from the output means of said up and down ramp modules, said sound generator creating an audio output signal,
   i) speaker means receiving said audio output signal and generating audible sound,
   j) an ion generator module having a line input and activated by a control signal from said clock module or said sleep function module, and thereby toggle an ion generator output signal on and off,
   k) ion generator means adapted to be toggled on and off by said ion generator output signal, said ion generator means adapted to provide exposure of said individual to a stream of ionized air, and
   l) housing means for protectively enclosing the aforesaid elements a through k.

2. The system of claim 1 further provided with switch means for overriding control of said lamp, speaker means and ion generator means.

* * * * *